United States Patent
Aoyagi et al.

(10) Patent No.: US 12,144,625 B2
(45) Date of Patent: Nov. 19, 2024

(54) PUNCTURE NEEDLE, PUNCTURE DEVICE, AND BLOOD SAMPLING DEVICE

(71) Applicants: THE SCHOOL CORPORATION KANSAI UNIVERSITY, Osaka (JP); AIKI RIOTECH CORPORATION, Aichi (JP)

(72) Inventors: Seiji Aoyagi, Osaka (JP); Hajime Matsumoto, Aichi (JP)

(73) Assignees: The School Corporation Kansai University, Osaka (JP); Aiki Riotech Corporation, Aichi (JP)

(*) Notice: Subject to any disclaimer, the term of this patent is extended or adjusted under 35 U.S.C. 154(b) by 703 days.

(21) Appl. No.: 17/283,826

(22) PCT Filed: Oct. 9, 2019

(86) PCT No.: PCT/JP2019/039741
§ 371 (c)(1),
(2) Date: Apr. 8, 2021

(87) PCT Pub. No.: WO2020/075735
PCT Pub. Date: Apr. 16, 2020

(65) Prior Publication Data
US 2021/0315495 A1    Oct. 14, 2021

(30) Foreign Application Priority Data
Oct. 12, 2018  (JP) .................. 2018-193782

(51) Int. Cl.
*A61B 5/00* (2006.01)
*A61B 5/151* (2006.01)
(52) U.S. Cl.
CPC .................. *A61B 5/151* (2013.01)

(58) Field of Classification Search
CPC ........ A61M 2005/3289; A61M 5/3286; A61M 5/329; A61M 5/3276; A61M 5/158;
(Continued)

(56) References Cited

U.S. PATENT DOCUMENTS

| | | |
|---|---|---|
| 3,058,369 A | 10/1962 | Vogel |
| 5,266,359 A | 11/1993 | Spielvogel |

(Continued)

FOREIGN PATENT DOCUMENTS

| | | |
|---|---|---|
| DE | 2012227 A1 | 9/1971 |
| DE | 19548593 A1 | 7/1997 |

(Continued)

OTHER PUBLICATIONS

Abraham, N. (Oct. 16, 2016). What is a hypodermic needle?. Medical Design and Outsourcing. https://www.medicaldesignandoutsourcing.com/what-is-a-hypodermic-needle/. (Year: 2016).*

(Continued)

*Primary Examiner* — May A Abouelela
(74) *Attorney, Agent, or Firm* — Verrill Dana, LLP

(57) ABSTRACT

Provided is a puncture needle that receives lower puncture resistance than conventional techniques. A puncture needle in accordance with an aspect of the present invention includes a needle body (10) that includes a main portion (12) and a distal portion (11) tapering from the main portion (12) and that is rotatable about a central axis (1) of the needle body (10), the needle body (10) including needle parts (15) separated by a boundary along the central axis, each of the needle parts (15) being independently translatable along the central axis (1).

9 Claims, 10 Drawing Sheets

(58) Field of Classification Search
CPC ... A61B 5/151; A61B 5/1519; A61B 5/15192; A61B 5/150022; A61B 5/15016; A61B 5/150229; A61B 5/150396; A61B 5/150511; A61B 5/150946; A61B 5/15115
See application file for complete search history.

(56) References Cited

U.S. PATENT DOCUMENTS

| | | | |
|---|---|---|---|
| 6,139,562 | A | 10/2000 | Mauze et al. |
| 7,901,363 | B2 | 3/2011 | Duchon et al. |
| 10,646,295 | B2 * | 5/2020 | Stoianovici ............ A61B 90/11 |
| 2010/0217155 | A1 * | 8/2010 | Poux ................ A61B 5/150022 |
| | | | 600/576 |
| 2015/0190587 | A1 | 7/2015 | Peh et al. |
| 2016/0067739 | A1 | 3/2016 | Jones |
| 2018/0043093 | A1 * | 2/2018 | Nakagami ......... A61M 25/0693 |
| 2019/0076186 | A1 * | 3/2019 | Fischell ............ A61B 18/1492 |
| 2021/0220570 | A1 * | 7/2021 | Keiser-Nielsen ... A61M 5/3286 |
| 2021/0275781 | A1 * | 9/2021 | Rebolledo Berríos ..................... |
| | | | A61M 25/06 |

FOREIGN PATENT DOCUMENTS

| | | |
|---|---|---|
| FR | 2269001 A1 | 11/1975 |
| JP | 64002877 A | 1/1989 |
| JP | 05-317324 A | 12/1993 |
| JP | 2005-317324 A | 12/1993 |
| JP | 09229157 A | 9/1997 |
| JP | 1999-309134 B2 | 9/1999 |
| JP | 2001-082568 A | 3/2001 |
| JP | 2004-057516 A | 2/2004 |
| JP | 2004-073298 A | 3/2004 |
| JP | 2006-521886 A | 9/2006 |
| JP | 2015-100889 A | 6/2015 |
| JP | 2017-000620 A | 1/2017 |
| WO | 2020/075736 A1 | 4/2020 |

OTHER PUBLICATIONS

International Preliminary Report on Patentability, PCT/US2019/039742 dated Apr. 22, 2021, 8 pgs.
International Search Report, PCT/US2019/039742 dated Dec. 24, 2019, 2 pgs.
International Preliminary Report on Patentability, PCT/US2019/039741 dated Apr. 22, 2021, 6 pgs.
International Search Report, PCT/US2019/039741 dated Jan. 7, 2020, 2 pgs.
Yamada et al. "Proposal of New Blood Sampling Method Using Microneedle—Use of Reciprocating Rotation, Visualization of Blood Vessels," Copyright 2018 JSPE, 2 pgs.
Extended European Search Report for 19870502.2-1122 / 3865064 PCT/JP2019039741 dated Jun. 28, 2022, 7 pgs.

* cited by examiner

FIG. 2
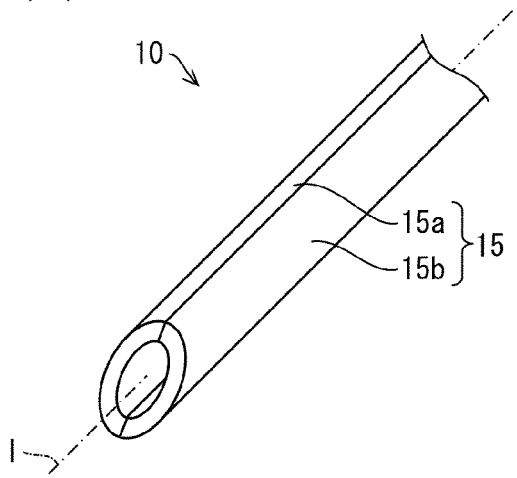
(a)
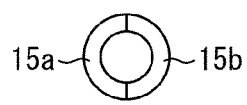
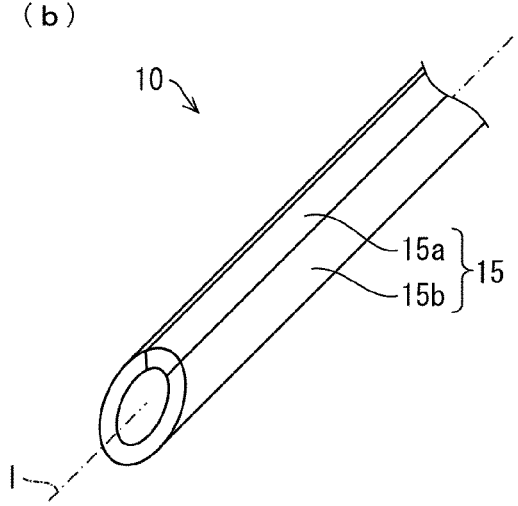
(b)
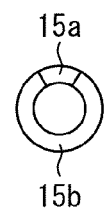
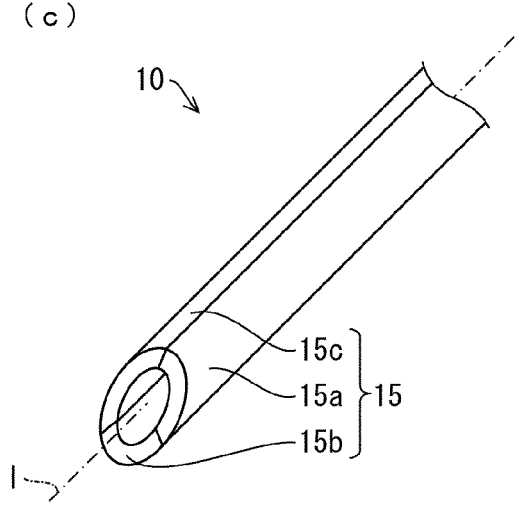
(c)
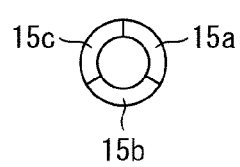

FIG. 3
(a)
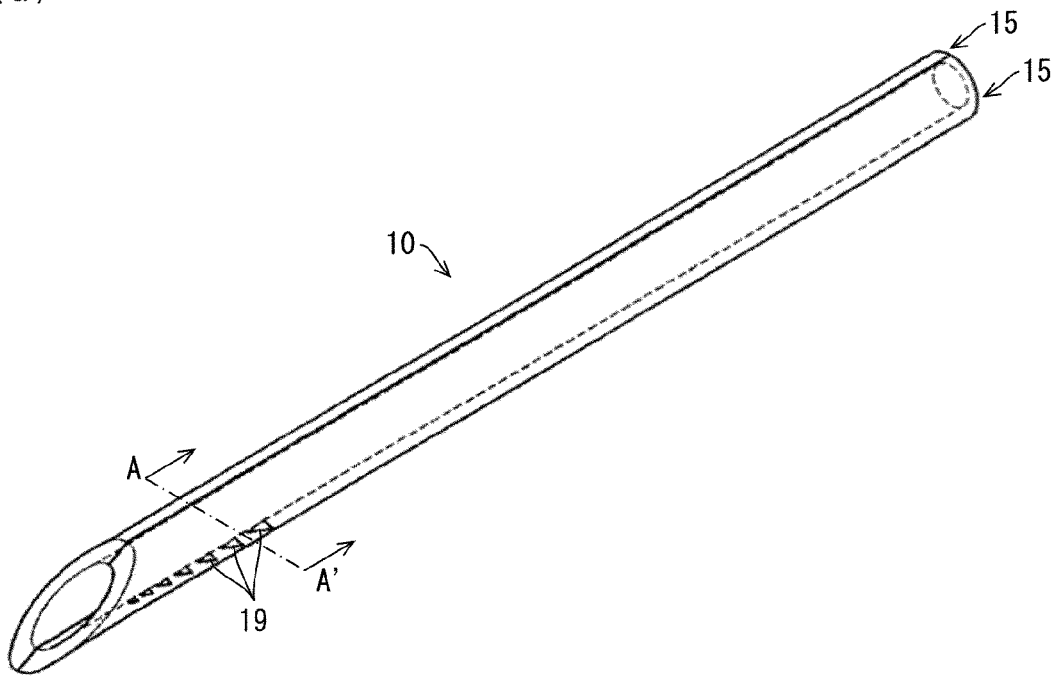
(b)
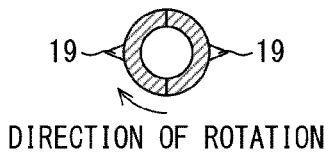
DIRECTION OF ROTATION
FIG. 4
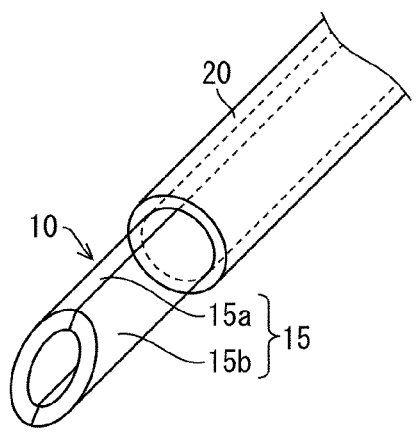

PUNCTURE NEEDLE, PUNCTURE DEVICE, AND BLOOD SAMPLING DEVICE

TECHNICAL FIELD

The present invention relates to a puncture needle, a puncture apparatus that includes the puncture needle, and a blood collecting apparatus that includes the puncture needle.

BACKGROUND ART

There are some situations in which, when a puncture needle is inserted into a subject to be punctured (hereinafter "to-be-punctured subject"), the puncture resistance that the puncture needle receives from the to-be-punctured subject is an issue. An example would be the situation in which a puncture needle is inserted into the skin of a test subject. Skin tissue has a layered structure composed of horny layer, epidermis, derma, and subcutaneous tissue arranged in the order named from the surface. Of such layers, the horny layer is stiff tissue (Young's modulus: about 1 MPa), whereas the subcutaneous tissue is soft tissue (Young's modulus: about 0.03 MPa). Therefore, when the puncture needle is caused to penetrate through the horny layer, a large puncture resistance is usually generated. There has been an issue in that, as a result of this, the skin tissue is squeezed from the point of contact with the puncture needle, and pain nerves are stimulated and/or blood flow is blocked.

The inventors of the present invention disclose, in Patent Literature 1, the following puncture needle as one measure to solve the above issue: a puncture needle including a needle body which is to be inserted into the skin, which includes a tapered distal portion, which has a passage that allows a fluid to flow therein, and which includes teeth aligned at least in the distal portion of the needle body, wherein the needle body includes needle parts arranged such that they are adjacent to each other along a direction perpendicular to the center line, and the needle parts include a main portion extending along the center line, a sharp portion tapering and extending from an end of the main portion, and a passage forming part that extends along the center line and that forms a part of the passage.

The inventors of the present invention further disclose, in Non-patent Literature 1, the technique of carrying out puncture while rotating a single needle with a motor, as another measure to solve the above issue.

CITATION LIST

Patent Literature

Patent Literature 1

Japanese Patent Application Publication, Tokukai, No. 2017-000620

Non-Patent Literature

Non-patent Literature 1

Masahiro YAMADA, Seiji AOYAGI, et al. "Proposal of new blood sampling method using microneedle—use of reciprocating rotation, visualization of blood vessels—" Technical papers of 2018 JSPE Spring Meeting, The Japan Society for Precision Engineering, 2018, pp. 531-532

SUMMARY OF INVENTION

Technical Problem

However, the foregoing conventional techniques still have room for a reduction in puncture resistance that the puncture needle receives.

Solution to Problem

In order to solve the above issue, a puncture needle in accordance with an aspect of the present invention includes a needle body that includes a main portion and a distal portion tapering from the main portion and that is rotatable about a central axis of the needle body, and is configured such that the needle body includes needle parts which are separated by a boundary along the central axis, and each of the needle parts is independently translatable along the central axis.

Advantageous Effects of Invention

An aspect of the present invention provides a puncture needle that receives lower puncture resistance than conventional techniques.

BRIEF DESCRIPTION OF DRAWINGS (a) of FIG. 1 is a perspective view of a needle body in accordance with an embodiment of the present invention. (b) of FIG. 1 is an exploded view of the needle body in (a) of FIG. 1. (c) of FIG. 1 is a perspective view of a needle body in accordance with another embodiment of the present invention. (d) of FIG. 1 is an exploded view of the needle body in (c) of FIG. 1.

(a) to (c) of FIG. 2 illustrate needle parts in accordance with an embodiment of the present invention. In each of the drawings, the upper panel is a perspective view, and the lower panel is a cross-sectional view taken along a plane perpendicular to the central axis of the needle body.

(a) of FIG. 3 is a perspective view illustrating a distal portion of a needle body in accordance with a further embodiment of the present invention. (b) of FIG. 3 is across-sectional view of (a) of FIG. 3.

FIG. 4 is a perspective view of a needle body and a sheath in accordance with an embodiment of the present invention.

FIG. 5 schematically illustrates why puncture resistance is reduced by the projecting motion of needle parts. (a) of FIG. 5 illustrates a puncture needle in accordance with an embodiment of the present invention (needle body is composed of two needle parts), and (b) of FIG. 5 illustrates a puncture needle in accordance with a conventional technique.

FIG. 6 is a block diagram illustrating a main part of a puncture apparatus in accordance with an aspect of the present invention.

(a) of FIG. 7 is a transition diagram illustrating the rotational motion of a needle body in accordance with an embodiment of the present invention. (b) of FIG. 7 is a transition diagram illustrating the rotational motion of a needle body in accordance with another embodiment of the present invention.

(a) of FIG. 8 is a transition diagram illustrating the projecting motion of needle parts in accordance with an embodiment of the present invention. (b) and (c) of FIG. 8 are transition diagrams illustrating examples of motions of needle parts, not included in the scope of the present invention.

DESCRIPTION OF EMBODIMENTS

Figure 1:
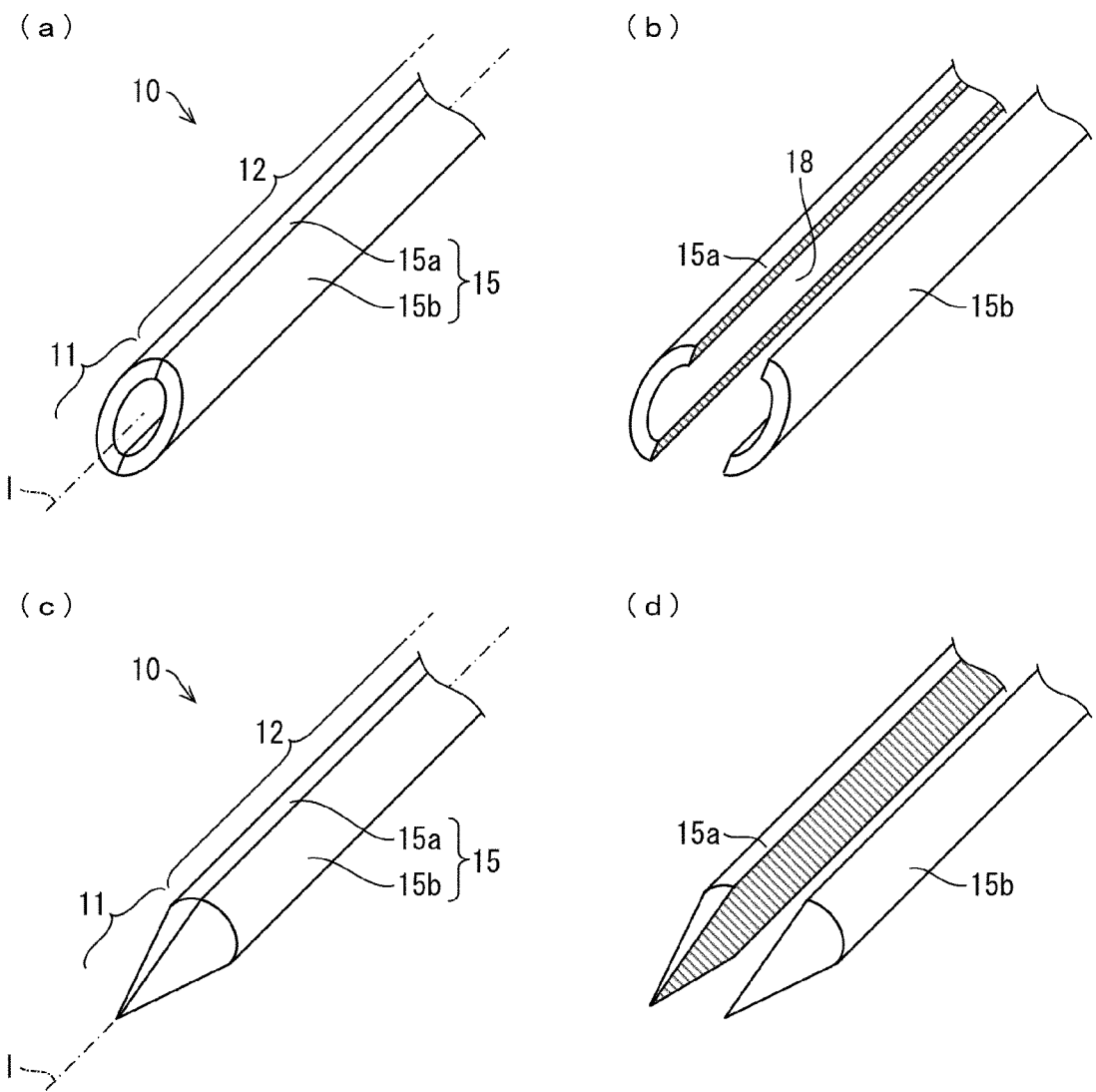

A needle body 10 in accordance with an aspect of the present invention is configured such that (i) the needle body 10 is rotatable about a central axis 1 of the needle body and (ii) needle parts 15 are each translatable along the central axis 1. For use of such a needle body 10, a puncture apparatus 100 in accordance with an aspect of the present invention is capable of causing the needle body 10 and the needle parts 15 to carry out the following motions: (i) causing the needle body 10 to rotate; and (ii) translating each of the needle parts 15 independently along the central axis 1, thereby causing at least one of the needle parts 15 to advance such that the at least one of the needle parts 15 projects forward relative to the other(s) of the needle parts 15. Such a needle body 10 and such a puncture apparatus 100 are effective in reducing puncture resistance. Therefore, the needle body 10 and the puncture apparatus 100 can be suitably applied to a blood collecting apparatus 200 in accordance with an aspect of the present invention.

Note that, in the present specification, out of the motions caused by the puncture apparatus, the motion (i) may be referred to as "rotational motion" and the motion (ii) may be referred to as "projecting motion".

The following description will more specifically discuss the present invention on the basis of Embodiments with reference to the drawings. However, the present invention is not limited to the independent embodiments. An embodiment derived from a combination of technical means each disclosed in a different embodiment is also encompassed in the technical scope of the present invention.

Embodiment 1: Puncture Needle

[Configuration of Needle Body and Needle Parts]

The following description will discuss a configuration of the needle body 10 and the needle parts 15 with reference to FIGS. 1 to 4.

As illustrated in FIG. 1, the needle body 10 includes a distal portion 11 and a main portion 12. The distal portion 11 tapers from the main portion 12. The distal portion 11 is a portion that makes contact with a to-be-punctured subject when the needle body 10 is inserted into the to-be-punctured subject.

The needle body 10 includes the needle parts 15. The needle parts 15 correspond to the needle body 10 divided along the central axis 1 of the needle body. Each of the needle parts 15 is independently translatable along the central axis 1 (this will be described later).

The needle body 10 illustrated in (a) and (b) of FIG. 1 has therein a flow passage 18 which is in communication with the outside environment of the needle body 10 and which allows a fluid to flow therein. The needle parts 15a and 15b here form a part of the flow passage 18 (in particular, see (b) of FIG. 1). This configuration makes it possible to use the needle body 10 as an injection needle. Specifically, it is possible to inject a fluid into the to-be-punctured subject through the needle body 10 and to collect a fluid from the to-be-punctured subject through the needle body 10.

(a) and (b) of FIG. 1 illustrate an injection needle having a typical shape. However, the specific shape of the needle body 10 is not limited, provided that there is the flow passage 18. For example, the flow passage 18 may be in communication with the outside environment of the needle body 10 through an opening in the side face of the distal portion 11, as disclosed in Patent Literature 1. However, the structure as illustrated in (a) and (b) of FIG. 1, i.e., the structure in which the flow passage 18 is in communication with the outside environment of the needle body 10 at the tip of the distal portion 11, is preferred because such a needle body 10 (and needle parts 15) is easier to produce. That is, the above structure is preferred because the needle body 10 and the needle parts 15 can be formed by splitting a typical injection needle.

Note that the structure of the needle body 10 may be a solid structure having no flow passage 18, as illustrated in (c) and (d) of FIG. 1.

Applications of the needle body 10 include not only the injection needle but also the following: (i) a lancet needle (which is to be inserted into the skin and cause the skin to ooze blood for, for example, testing blood sugar level); (ii) a needle for drug delivery (for example, a drug can be applied to the surface of the needle or can be supported in a recess in the needle); (iii) a needle for perforation (which can be used when, for example, operating on the brain or an organ); and (iv) a needle for injection of a fluid (which can be used when, for example, injecting a fluid [such as a liquid ink] serving as a marker during surgery into the surface of an organ).

The applications of the needle body 10 are not limited to life science or medical care. Examples of such applications include (i) a needle for perforating a tree (for example, a nutrient solution or an agricultural chemical can be injected into a tree); and (ii) drilling in civil engineering (the needle body 10 can also be used as a boring instrument, provided that the sizes and shapes of the needle body 10 and the needle parts 15 are set appropriately).

The following description will discuss an example of the configuration of the needle parts 15 in more detail with reference to FIG. 2. As described earlier, the needle parts 15 correspond to the needle body 10 divided along the central axis 1 of the needle body. (a) of FIG. 2 illustrates an example of the configuration of the needle parts 15 which correspond to the needle body 10 divided in half along the central axis 1 ((a) of FIG. 2 corresponds to the needle body 10 as illustrated in (a) of FIG. 1). (b) of FIG. 2 illustrates an example of the configuration of the needle parts 15 in which the needle part 15a is smaller than the needle part 15b. (c) of FIG. 2 illustrates an example of the configuration of the needle parts 15 which correspond to the needle body divided in three parts: needle parts 15a, 15b, and 15c.

As is apparent from the above-mentioned drawings, the following holds for the "needle parts 15 which are separated by a boundary along the central axis 1": "the boundary surface between adjacent needle parts 15 is parallel to (or substantially parallel to) the direction of the central axis 1 of the needle body". Needless to say, the boundary surface between adjacent needle parts 15 may not be perfectly parallel to the direction of the central axis 1 of the needle body and may not be flat, provided that the projecting motion of the needle parts 15 is available.

The needle parts 15 which correspond to the needle body 10 divided in half along the central axis 1 as illustrated in (a) of FIG. 2 is preferred in that the needle parts 15 are easy to produce. Furthermore, in order to enhance the effect of reducing puncture resistance brought about by the projecting motion of the needle parts 15, it is preferable that at least one boundary surface between adjacent needle parts 15 pass through the tip of the distal portion 11. That is, it is preferable that a boundary surface between needle parts 15 be present at the sharp point of the tip of the needle body 10.

Furthermore, in a case where the needle body 10 has the flow passage 18, the needle parts 15 are preferably arranged such that they are adjacent to each other in a cross section perpendicular to the central axis 1 (see the lower panels of (a), (b), and (c) of FIG. 2). When the needle parts 15 are arranged as such, there will be no gaps between the adjacent needle parts 15. This makes it possible to allow a fluid to flow within the flow passage 18 without leakage. Note, however, that, depending on the physical properties (such as viscosity, surface tension) of the fluid which flows within the flow passage 18, even if there is a small gap between adjacent needle parts 15, the fluid can flow within the flow passage 18 without leakage.

[Surface and Shape of Distal Portion]

The surface profile of the needle body 10 is not particularly limited. In an embodiment, the surface of the needle body 10 which surface makes contact with the to-be-punctured is smooth at least in the distal portion 11 (see FIG. 1). In another embodiment, the surface of the needle body 10 which surface makes contact with the to-be-punctured subject has teeth 19 at least in the distal portion 11 (see (a) of FIG. 3).

In a case where the surface of the needle body 10 which surface makes contact with the to-be-punctured subject is smooth, it is possible to further reduce the friction between the surface and the to-be-punctured subject that would be generated during the rotational motion of the needle body 10. This makes it possible for the needle body 10, stuck in the to-be-punctured subject, to rotate smoothly. In this regard, when the teeth 19 are provided, the friction between the surface and the to-be-punctured subject that would be generated during the rotational motion of the needle body 10 tends to become large (see (b) of FIG. 3). Furthermore, the structure of the needle body 10 (and needle parts 15) is simpler, and therefore the needle body 10 is easier to produce.

On the contrary, a configuration in which the surface of the needle body 10 which makes contact with the to-be-punctured subject is provided with teeth is advantageous when the needle parts 15 are caused to carry out projecting motion. Specifically, the teeth 19 are capable of tearing the to-be-punctured subject and getting caught in the to-be-punctured subject when the needle parts 15 carry out projecting motion. Therefore, puncture proceeds step by step, and the effect of reducing puncture resistance is expected.

As has been described, the phrase "a surface is smooth" in the present specification can be described as "a surface has no projections" such as the teeth 19.

There is no particular limitation on the shape of the distal portion 11 of the needle body 10 in a cross section perpendicular to the central axis 1. The cross section may be in the form of, for example, a circle or an arc (in such cases, the distal portion 11 has the shape as illustrated in (a) or (c) of FIG. 1) or a polygon or a star etc. (in such cases, the needle body 10 has the shape of a prism). The needle body 10 in the form of a cylinder is easy to produce, because the structure is simple. On the other hand, the needle body 10 in the form of a prism is capable of concentrating stress applied to the to-be-punctured subject, and therefore is capable of reducing puncture resistance. This effect is more likely to appear in cases where the needle body 10 has more vertices.

[Other Configuration]

In a case the needle body 10 has the flow passage 18, a sheath 20 which at least partially covers the needle body 10 is preferably further provided, as illustrated in FIG. 4. The sheath 20 here is provided in a proximal portion (opposite the distal portion 11) of the needle body 10. Providing the sheath 20 makes it possible to prevent the fluid from flowing out of the flow passage 18 even when the needle parts 15a and 15b are caused to carry out projecting motion.

Note, however, that it is possible to prevent the fluid from flowing out even without the sheath 20, provided that the gap between the needle parts 15a and 15b is designed small enough in consideration of physical properties (such as viscosity, surface tension) of the fluid flowing within the flow passage 18.

The material and dimensions of the needle body 10 can be selected as appropriate. For example, the material of the needle body 10 is a silicone resin, a polymer (such as polylactic acid, polycarbonate, epoxy resin, or acrylic resin, fluororesin), or a metal (such as nickel, titanium, iron, stainless steel, tungsten, molybdenum, aluminum, or copper). A configuration in which the surface of the needle body 10 is covered with another material can be employed (for example, in a case where the needle body 10 is made of a material not biocompatible such as nickel, the surface of the needle body 10 is preferably coated with Teflon (registered trademark) or the like). The outer diameter of the needle body 10 may be about 30 μm to about 200 μm, and the length of the needle body 10 may be about 1000 μm to about 3000 μm.

[Reduction of Puncture Resistance]

The needle body 10 is rotatable about the central axis 1. Furthermore, each of the needle parts 15 is independently translatable along the central axis 1. As a result, the needle body 10 is capable of carrying out rotational motion and projecting motion which will be described in Embodiment 2. The use of the needle body 10 carrying out such motions reduces the puncture resistance that is generated when the needle body 10 is inserted into the to-be-punctured subject, as compared to conventional techniques.

The following description discusses the effect of reducing puncture resistance brought about by the needle body 10.

Figure 5:
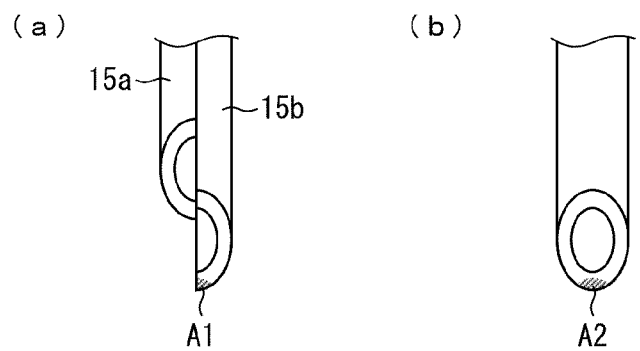

FIG. 5 schematically illustrates (a) the needle body 10 in accordance with Embodiment 1 and (b) a puncture needle in accordance with a conventional technique, which are compared with each other. The needle body 10 is divided in the needle parts 15 (in FIG. 5, needle parts 15a and 15b), and the needle parts 15 carry out projecting motion. Therefore, the area of contact A1 between the needle body 10 and the to-be-punctured subject is small (compared with the area of contact A2 between the puncture needle and the to-be-punctured subject in the puncture needle in accordance with the conventional technique). As a result, stress acting on the to-be-punctured subject is concentrated in a small area. Furthermore, since the needle body 10 is divided in needle parts 15, the distal portion 11 has a sharper structure. This is the effect of reducing puncture resistance brought about by the needle body 10 divided in the needle parts 15 and causing the needle parts 15 to carry out projecting motion.

Furthermore, the area which makes contact with the to-be-punctured subject when the puncture needle carries out rotational motion is also smaller in the needle 10 of Embodiment 1 than in the puncture needle of the conventional technique (see A1 in comparison to A2). This results in a reduction in friction between the needle and the to-be-punctured subject, and the rotational motion becomes smoother.

In an aspect, the present invention is based on the following finding: the combination of such projecting motion and rotational motion makes it possible to reduce puncture resistance to a much greater extent than each motion alone.

The harder the to-be-punctured subject is, the greater the puncture resistance will be. In skin tissue, the horny layer is harder than the other tissues. Therefore, in cases where the skin tissue is a to-be-punctured subject, most of the puncture resistance is regarded as puncture resistance that is generated when the horny layer is perforated. That is, the use of a puncture needle in accordance with an embodiment of the present invention makes it easy to perforate the horny layer (makes it easy to insert the needle). Therefore, even if a puncture needle having a known shape and carrying out known motion is used after the horny layer is perforated, it can be said that the effect of the present invention, i.e., "reduction in puncture resistance", is brought about.

Embodiment 2: Puncture Apparatus

[Configuration of Puncture Apparatus]

Figure 6:
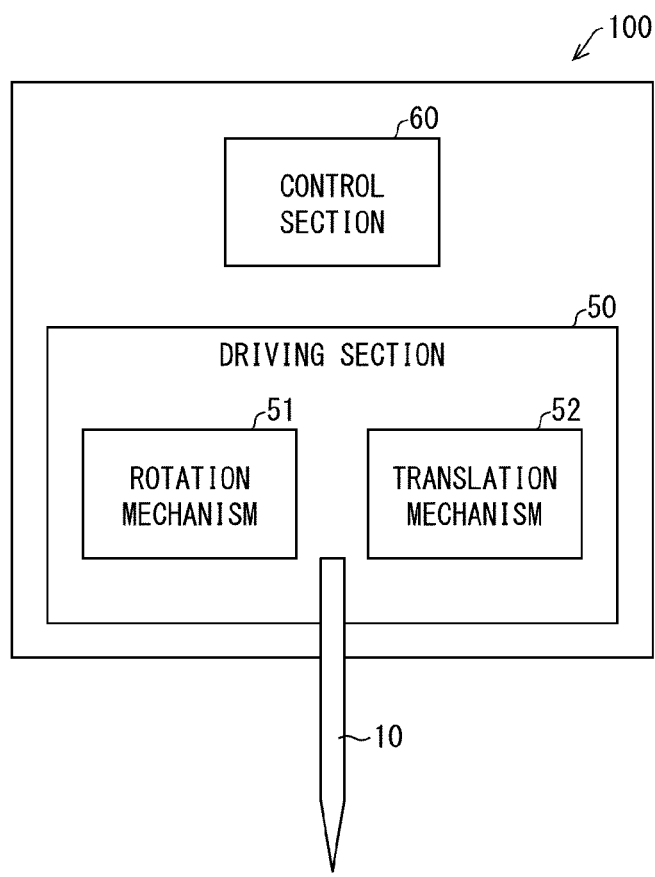

FIG. 6 is a block diagram illustrating a main part of a puncture apparatus in accordance with an aspect of the present invention. A puncture apparatus 100 includes a needle body 10 and a driving section 50.

The configuration of the needle body 10 has been described in Embodiment 1. The needle body 10 may be detachable from the puncture apparatus 100.

The driving section 50 drives the needle body 10 to carry out rotational motion while driving the needle parts 15 to carry out projecting motion. The driving section 50 includes a rotation mechanism 51 and a translation mechanism 52. The rotation mechanism 51 causes the needle body 10 to rotate about the central axis 1. The translation mechanism 52 translates each of the needle parts 15 independently along the central axis 1. With this, the translation mechanism 52 causes at least one of the needle parts 15 to advance such that the at least one of the needle parts 15 projects forward relative to the other(s) of the needle parts 15.

The rotation mechanism 51 and the translation mechanism 52 can be constituted by a combination of known mechanisms. For example, electric actuators (such as piezoelectric ceramics, motors, solenoids, and/or the like) can be used as the rotation mechanism 51 and the translation mechanism 52. Besides those listed above, for example, actuators powered by hydraulic pressure, air pressure, or magnetic force may be used. A combination of mechanical components such as a rack and pinion, a ball screw, and/or the like may be used. All or a portion of the rotation and translation mechanisms 51 and 52 may be constituted by a single mechanism.

The puncture apparatus 100 may include a control section 60. The control section 60 is a functional block that controls the operation of the driving section 50 to thereby control the position and motion of the needle body 10 (and the needle parts 15). The control section 60 can be realized by a logic circuit (hardware) provided in an integrated circuit (IC chip) or the like or can be alternatively realized by software.

In a case where the control section 60 is realized by software, the puncture apparatus 100 includes a computer that executes instructions of a program that is software realizing the foregoing functions. The computer, for example, includes at least one processor and at least one computer-readable storage medium storing the program. An object of the present invention can be achieved by the processor of the computer reading and executing the program stored in the storage medium. Examples of the processor encompass a central processing unit (CPU). Examples of the storage medium encompass a "non-transitory tangible medium" such as a read only memory (ROM), a tape, a disk, a card, a semiconductor memory, and a programmable logic circuit. The computer may further include a random access memory (RAM) or the like in which the program is loaded. Further, the program may be made available to the computer via any transmission medium (such as a communication network and a broadcast wave) which allows the program to be transmitted. Note that an aspect of the present invention can also be achieved in the form of a computer data signal in which the program is embodied via electronic transmission and which is embedded in a carrier wave.

[Motions of Needle Body and Needle Parts]

The following description will discuss motions of the needle body 10 and the needle parts 15 with reference to FIGS. 7 to 10. The needle body 10 is rotatable about the central axis 1. Each of the needle parts 15 is independently translatable along the central axis 1. Therefore, the driving section 50 is capable of causing the needle body 10 to carry out rotational motion and causing the needle parts 15 to carry out projecting motion.

(Rotational Motion)

Figure 7:
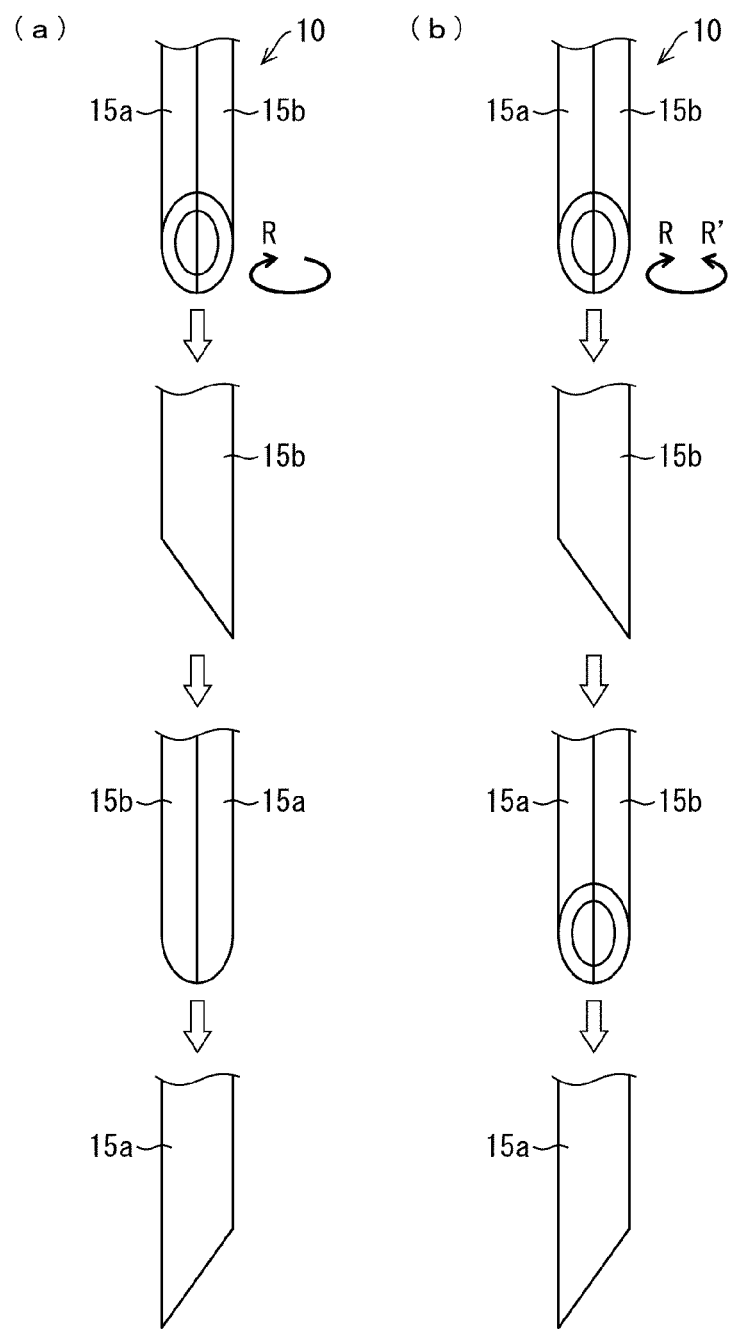

FIG. 7 is a transition diagram illustrating the rotational motion of the needle body 10. In (a) of FIG. 7, the needle body 10 rotates in direction R (which is a clockwise direction). On the contrary, in (b) of FIG. 7, the needle body 10 rotates in the direction R and rotates in direction R' (which is a counterclockwise direction) alternately. More specifically, the needle body 10 illustrated in (b) of FIG. 7 first rotates by 90° in the direction R and then rotates by 90° in the direction R'. Attention should be focused on the fact that, in the third panels of (a) and (b) of FIG. 7, the needle body 10 faces backward in (a) of FIG. 7 and faces forward in (b) of FIG. 7.

In the present invention, the rotational motion of the needle body 10 may be unidirectional rotational motion as illustrated in (a) of FIG. 7 or may be rotational motion in which the needle body 10 rotates in opposite directions alternately as illustrated in (b) of FIG. 7. Note that, in a case where the needle body 10 carries out unidirectional rotational motion, the needle body 10 may rotate in the direction (direction R') opposite to the direction as shown in (a) of FIG. 7.

In a case where the needle body 10 rotates in one direction, there is a possibility that the to-be-punctured subject would be wrapped around the needle body 10. As a result, for example, in a case where the needle body 10 is inserted in the skin, the needle body 10 may stimulate a pain nerve. In order to prevent such an event from occurring, an aspect in which the needle body 10 rotates in opposite directions alternately is preferred. That is, the rotational motion of the needle body 10 is preferably the aspect as shown in (b) of FIG. 7.

The rotation speed of the needle body 10 can be set as appropriate. In an aspect in which the needle body 10 rotates in opposite directions alternately, the angle of rotation of the needle body 10 can also be set as appropriate. The rotation speed and/or the angle of rotation of the needle body 10 may be varied during one puncture session. For example, the angle of rotation may differ between when the needle body 10 rotates in the direction R and when the needle body 10 rotates in the direction R'.

(Projecting Motion)

Figure 8:
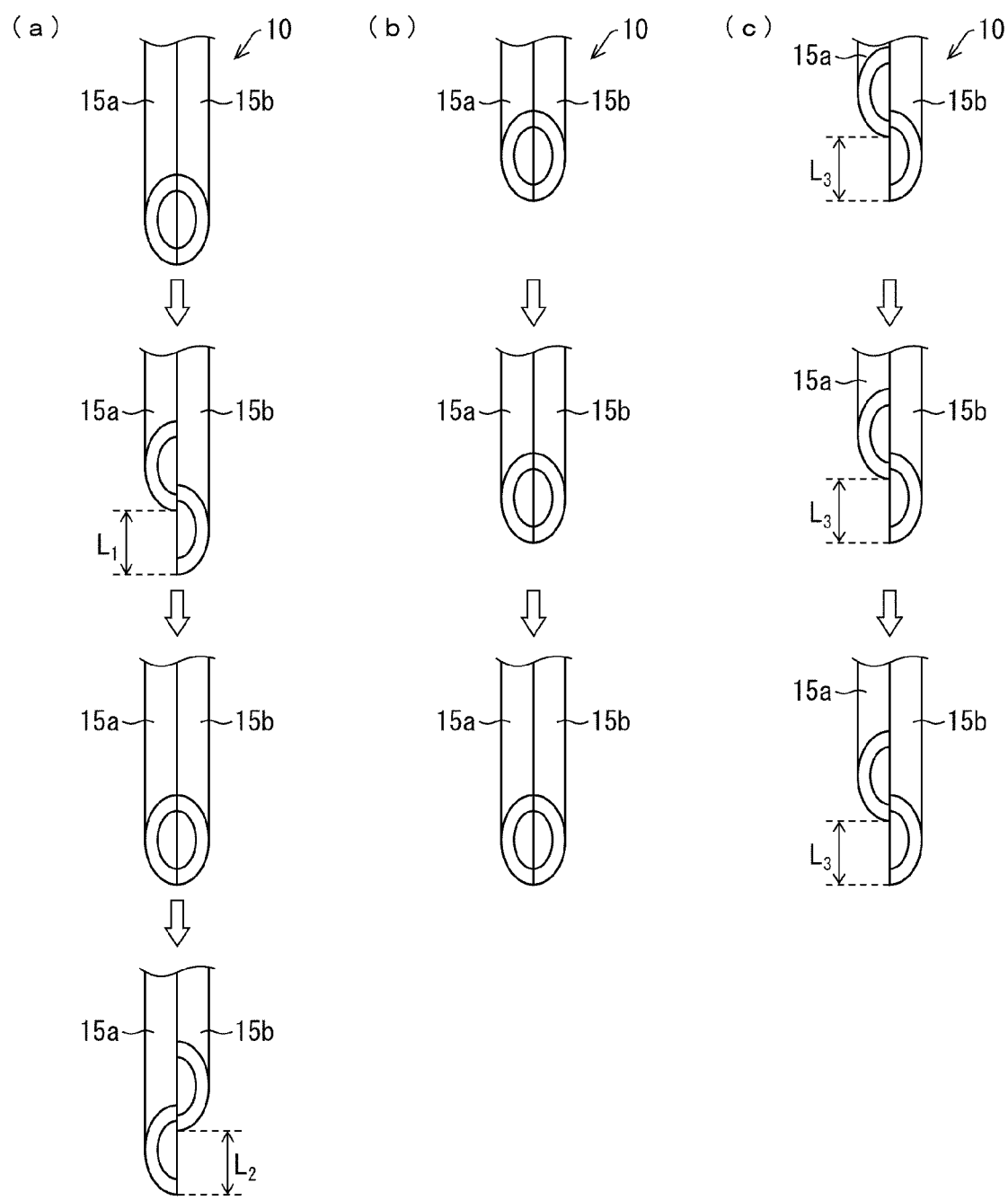

(a) of FIG. 8 is a transition diagram illustrating projecting motion. In (a) of FIG. 8, the needle parts 15a and 15b advance along the central axis 1 such that the needle parts 15a and 15b alternately project forward relative to each other.

In the first panel of (a) of FIG. 8, the needle parts 15a and 15b are arranged such that their tips are aligned with each other. In the second panel, the needle part 15b has advanced along the central axis 1 and projected forward relative to the needle part 15a by L1. In the third panel, the needle part 15a has advanced along the central axis 1 and the tips of the needle parts 15a and 15b have become aligned with each other again. In the fourth panel, the needle part 15a has further advanced along the central axis 1 and projected forward relative to the needle part 15b by L2.

As such, during the projecting motion, the projection of the needle part 15a and the projection of the needle part 15b are repeated alternately. Specifically, one of the needle parts 15a and 15b, e.g., the needle part 15a, advances such that it projects forward relative to the other of the needle parts 15a and 15b, e.g., the needle part 15b, and then the needle part 15b advances such that it projects forward relative to the needle part 15a. Such actions are repeated. The needle parts 15a and 15b alternately carry out reciprocating motions.

It is noted here that the projection of the needle part 15a may be relative projection. That is, the needle part 15a may be caused to project by withdrawing the needle part 15b instead of advancing the needle part 15a. Therefore, during the projecting motion, one of or some of the needle parts 15 may stay still. For example, the needle part 15b may be caused to project relative to the needle part 15a by withdrawing the needle part 15a while the needle part 15b is staying still. However, for achieving a simple configuration of the translation mechanism, a configuration in which all the needle parts 15 are translated is preferred.

Note that one or more of the needle parts 15 may be advanced while another one or more of the needle parts 15 are withdrawn. This is discussed below with reference to (a) of FIG. 8. Specifically, when the needle part 15a is advanced along the central axis 1 such that it projects forward, the needle part 15b may be withdrawn along the central axis 1 (the same applies to the needle part 15b).

During the projecting motion, the distance between the tip of the needle part 15a and the tip of the needle part 15b changes over time. One of the needle parts 15a and 15b projects relative to the other of the needle parts 15a and 15b and the other of the needle parts 15a and 15b projects relative to the one of the needle parts 15a and 15b, alternately, during the projecting motion. In contrast, the motions illustrated as examples in (b) and (c) of FIG. 8 are not included in the scope of the projecting motion. In (b) of FIG. 8, the needle parts 15a and 15b advance along the central axis 1 with their tips kept aligned with each other (with the distance between their tips kept at zero). In (c) of FIG. 8, the needle parts 15a and 15b advance along the central axis 1 with the distance L3 between the tip of the needle part 15a and the tip of the needle part 15b kept constant. Such motions are not included in the scope of the projecting motion.

(Combination of Rotational Motion and Projecting Motion)

Figure 9:
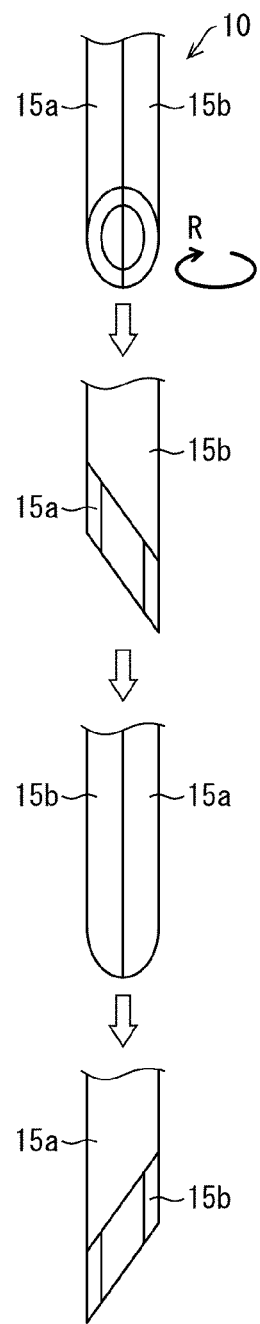
FIG. 9 is a transition diagram illustrating the motion of a needle body in accordance with an embodiment of the present invention.
Figure 10:
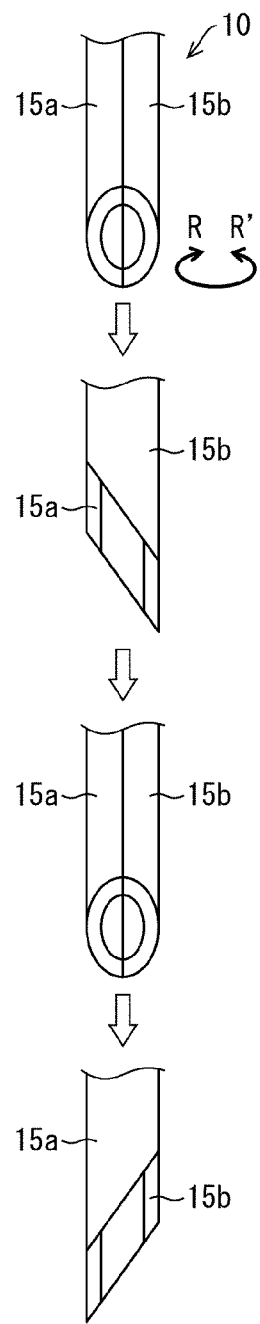
FIG. 10 is a transition diagram illustrating the motion of a needle body in accordance with another embodiment of the present invention.

Motion which is the combination of the foregoing rotational motion and projecting motion is the motion of the needle body 10 and the needle parts 15 in the puncture apparatus 100 in accordance with an aspect of the present invention. Examples of such motion are illustrated in FIGS. 9 and 10. FIG. 9 is a transition diagram illustrating motion which is the combination of unidirectional (direction R) rotational motion and projecting motion. FIG. 10 is a transition diagram illustrating motion which is the combination of (i) rotational motion in which rotation in the direction R and rotation in the direction R' are carried out alternately and (ii) projecting motion.

(Other Motions)

The translation mechanism 52 may cause the entire needle body 10 to move along the central axis 1. This motion makes it possible to cause the distal portion 11 of the needle body 10 to approach the to-be-punctured subject or to go away from the to-be-punctured subject. That is, this motion can be used when the needle body 10 is inserted into the to-be-punctured subject or when the needle body 10 is removed from the to-be-punctured subject. In such a case, the projecting motion is achieved by the combination of the alternating reciprocating motions of the respective needle parts 15 and the forward motion of the entire needle body 10.

By inserting the needle body 10 into the to-be-punctured subject while carrying out the combination of the above-described rotational motion and projecting motion, it is possible to reduce the puncture resistance associated with the insertion of the needle body 10.

Embodiment 3: Blood Collecting Apparatus

Figure 11:
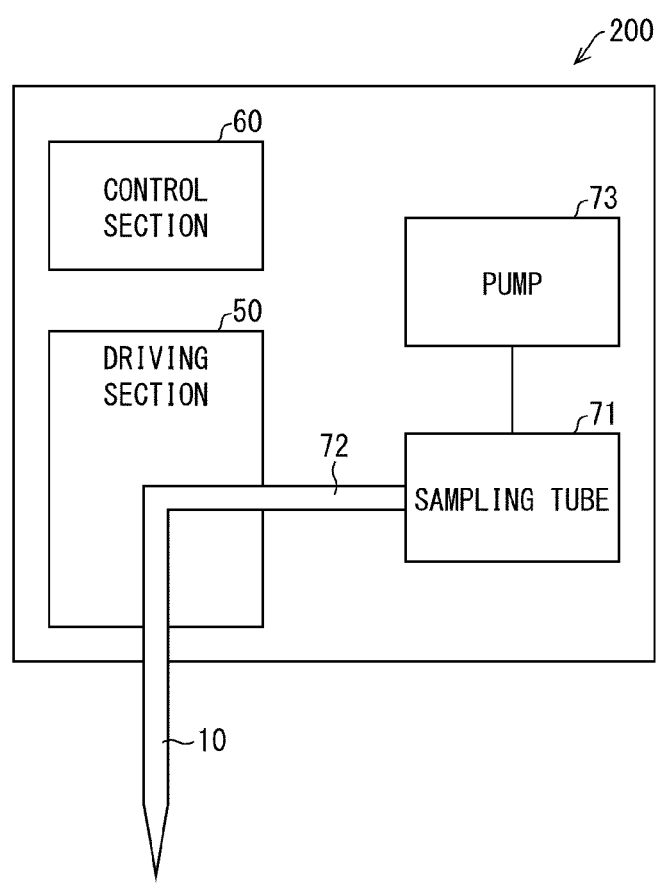
FIG. 11 is a block diagram illustrating a main part of a blood collecting apparatus in accordance with an aspect of the present invention.

FIG. 11 is a block diagram illustrating a main part of a blood collecting apparatus 200 in accordance with an aspect of the present invention. The blood collecting apparatus 200 includes the puncture apparatus 100 (needle body 10 and driving section 50) described in Embodiment 2. The needle body 10 of the blood collecting apparatus 200 includes the flow passage 18 so that blood can be collected through the needle body 10. The blood collecting apparatus 200 may include the control section 60. The control section 60 has already been described in Embodiment 2.

The blood collecting apparatus 200 may include: a sampling tube 71 in which collected blood is to be stored; a blood flow passage 72 through which the needle body 10 and the sampling tube 71 communicate; and a pump 73 for aspiration of blood to the sampling tube 71. In the blood collecting apparatus 200 configured as such, once the needle body 10 has been inserted into the skin and an opening of the flow passage 18 has reached a blood vessel, blood flows into the flow passage 18 through the opening. Then, the blood passes through the blood flow passage 72 and is stored in the sampling tube 71. Note that the collection of blood can be achieved by allowing the blood to spontaneously flow using blood pressure and/or capillary action, instead of the aspiration using the pump 73.

The needle body 10 may be detachable from the blood collecting apparatus 200. Similarly, the sampling tube 71 may be detachable from the blood collecting apparatus 200.

The needle body 10 is preferably a fine needle (for example, a needle having an outer diameter of about 30 μm to about 200 μm), in order to achieve the effect of reducing puncture resistance. Such a needle body 10 is suitable for collecting blood from an arteriola, a venula, and/or a capillary vessel. Furthermore, such a needle body 10 is suitable for collection of a small amount of blood (for example, about 0.3 μL to about 200 μL); therefore, the blood collecting apparatus 200 is suitable for use in analyses using a small amount of blood. Specific examples of such an application include measurement of blood sugar level.

[Variation]

The mode of motion of the needle body 10 and the needle parts 15 described in Embodiments 2 and 3 is the mode of motion which is the combination of rotational motion and projecting motion (such a mode of motion is referred to as "first motion mode"). However, the needle body 10 and the needle parts 15 can be driven in a motion mode in which rotational motion alone is carried out or in a motion mode in which projecting motion alone is carried out (such motion modes are collectively referred to as "second motion mode"). The puncture apparatus 100 in accordance with Embodiment 2 and the blood collecting apparatus 200 in accordance with Embodiment 3 are capable of driving the needle body 10 and the needle parts 15 in both the first motion mode and the second motion mode.

For example, in a case where the to-be-punctured subject is the skin, two different motion modes can be used when perforating the horny layer at the surface and when perforating the epidermis, derma, and subcutaneous tissue underneath the horny layer, respectively. For example, the needle body 10 may be moved in the first motion mode when perforating the horny layer, whereas the needle body 10 may be caused to carry out projecting motion alone (a kind of second motion mode) when perforating the tissue underneath the horny layer. The first motion mode is suitable for making a hole in a hard layer (horny layer). On the contrary, when the projecting motion alone is carried out, soft tissue (epidermis, derma, subcutaneous tissue) would not be wrapped around the needle body 10 by the rotational motion of the needle body 10. Therefore, the above-stated design is reasonable.

The matters described in the foregoing sections can apply as appropriate to other sections. The present invention is not limited to the foregoing embodiments, but may be altered in various ways within the scope of the claims. The present invention also encompasses, in its technical scope, any embodiment derived by combining technical means disclosed in differing embodiments.

All academic and patent documents cited in the present specification are incorporated herein by reference.

Aspects of the present invention can also be expressed as follows:

The present invention includes the following features.

<1>

A puncture needle including a needle body 10 that includes a main portion 12 and a distal portion 11 tapering from the main portion 12 and that is rotatable about a central axis 1 of the needle body 10,
the needle body 10 including needle parts 15 which are separated by a boundary along the central axis 1,
each of the needle parts 15 being independently translatable along the central axis 1.

<2>

The puncture needle described in <1>, in which a surface of the needle body 10 which surface makes contact with a subject to be punctured is a smooth surface at least in the distal portion 11.

<3>

The puncture needle described in <1> or <2>, in which:
the needle body 10 has therein a flow passage 18 which is in communication with an outside environment of the needle body 10 and which allows a fluid to flow therein; and
each of the needle parts 15 forms a part of the flow passage 18.

<4>

The puncture needle described in any one of <1> to <3>, further including a sheath 20 that at least partially covers the needle body 10,
the sheath 20 being provided in a proximal portion of the needle body 10.

<5>

A puncture apparatus 100 including a puncture needle described in any one of <1> to <3> and a driving section 50,
the driving section 50 including:
a rotation mechanism 51 configured to cause the needle body 10 to rotate; and
a translation mechanism 52 configured to translate each of the needle parts 15 independently along the central axis 1,
the translation mechanism 52 being configured to cause at least one of the needle parts 15 to advance such that the at least one of the needle parts 15 projects forward relative to the other one or more of the needle parts 15.

<6>

The puncture apparatus 100 described in <5>, in which the rotation mechanism 51 is configured to cause the needle body 10 to carry out clockwise rotational motion and counterclockwise rotational motion alternately.

<7>

The puncture apparatus described in <5> or <6>, in which the driving section 50 is configured to cause the needle body 10 to carry out the following two types of motion modes:

(i) first motion mode in which the needle body 10 is caused to rotate and at least one of the needle parts 15 is caused to advance such that the at least one of the needle parts 15 projects forward relative to the other one or more of the needle parts 15; and (ii) second motion mode in which the needle body 10 is caused to rotate or at least one of the needle parts 15 is caused to advance such that the at least one of the needle parts 15 projects forward relative to the other one or more of the needle parts 15.

<8>

A blood collecting apparatus 200 including a puncture needle described in <1> or <2> and a driving section 50,
the needle body 10 having therein a flow passage 18 which is in communication with an outside environment of the needle body 10 and which allows a fluid to flow therein,
each of the needle parts 15 forming a part of the flow passage 15,
the driving section 50 including
a rotation mechanism 51 configured to cause the needle body 10 to rotate; and
a translation mechanism 52 configured to translate each of the needle parts 15 independently along the central axis 1,
the translation mechanism 52 being configured to cause at least one of the needle parts 15 to advance such that the at least one of the needle parts 15 projects forward relative to the other one or more of the needle parts 15.

<9>
The blood collecting apparatus described in <8>, in which the rotation mechanism 51 is configured to cause the needle body 10 to carry out clockwise rotational motion and counterclockwise rotational motion alternately.

<10>
The blood collecting apparatus described in <8> or <9>, in which the driving section 50 is configured to cause the needle body 10 to carry out the following two types of motion modes:
(i) first motion mode in which the needle body 10 is caused to rotate and at least one of the needle parts 15 is caused to advance such that the at least one of the needle parts 15 projects forward relative to the other one or more of the needle parts 15; and
(ii) second motion mode in which the needle body 10 is caused to rotate or at least one of the needle parts 15 is caused to advance such that the at least one of the needle parts 15 projects forward relative to the other one or more of the needle parts 15.

EXAMPLES

The effect of reducing puncture resistance brought about by the combination of the rotational motion of a needle body and the projecting motion of needle parts was tested. Nanopass needle (34 G, 180 μm in diameter, manufactured by Terumo Corporation) was split along the direction of the central axis, and used as the needle body and the needle parts. The needle body was inserted into a to-be-punctured subject (artificial skin composed of agar and a keratin film disposed on the agar) with use of a uniaxial stage, and stress that was generated during the insertion was measured with a load cell. The measured stress was regarded as puncture resistance. The conditions under which the needle body and the needle parts carried out motions are as follows. Note that, in the measurement in which projections were carried out in-phase, the two needle parts were caused to carry out the in-phase projecting motions, instead of projecting alternately. In the measurement in which the combination of projecting motion and rotational motion was carried out, the conditions for both motions were used in combination.
Projecting Motion
  Frequency: 10 Hz, Amplitude: 0.1 mm
Rotational Motion
  Rotation direction: Rotation in clockwise direction and rotation counterclockwise direction are carried out alternately, rotation speed: 180 rpm, angle of rotation: 180°

Figure 12:
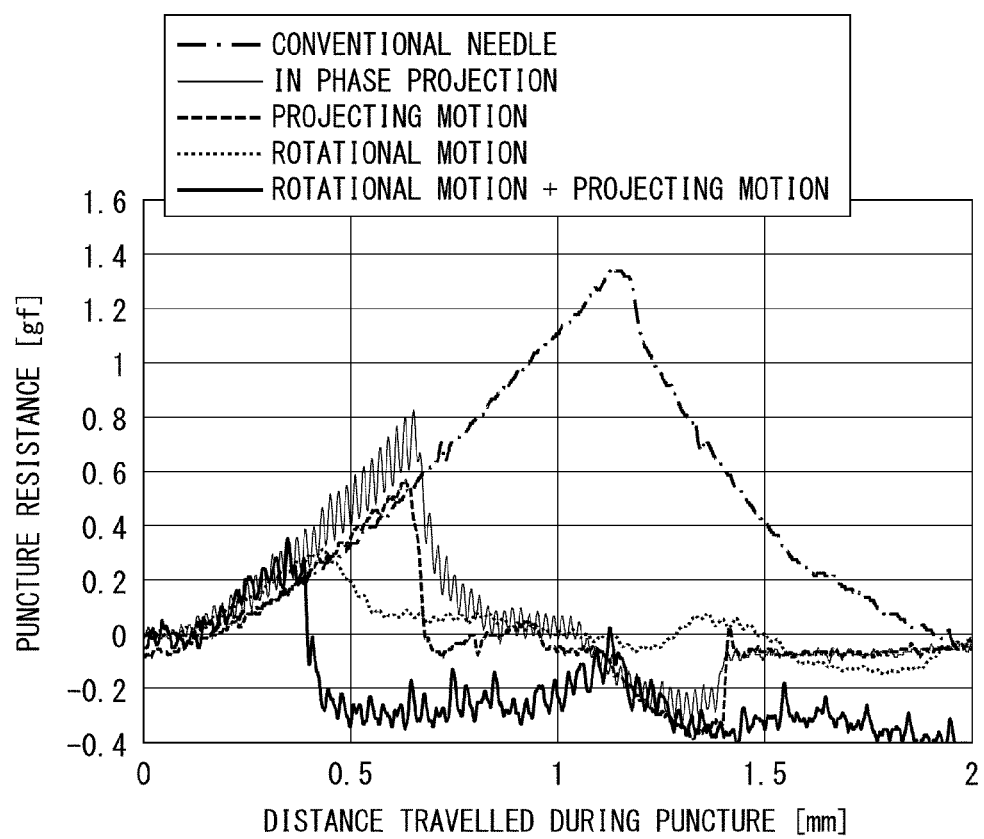
FIG. 12 is a chart in which the puncture resistance received by a puncture needle in accordance with an embodiment of the present invention is compared with that of a puncture needle in accordance with a conventional technique.

The results are shown in FIG. 12. As shown in FIG. 12, the needle body which carried out the in-phase projections and the needle bodies which carried out projecting motion alone or rotational motion alone were successful in reducing puncture resistance, as compared to a conventional puncture needle (which is not divided in needle parts and which carries out neither rotational motion nor projecting motion). Note, however, that the combination of two types of motions resulted in a further reduction in puncture resistance. The distance travelled before the puncture resistance abruptly decreases is also significantly small. This means that the needle body has penetrated the keratin film (corresponding to the horny layer of the real skin tissue) only after a smaller amount of translation than other needle bodies. This suggests that a puncture apparatus in accordance with an embodiment of the present invention makes it possible to reduce the pressure on the skin that would result from the puncture, and thus possible to alleviate the pain associated with the puncture.

REFERENCE SIGNS LIST

10 needle body
11 distal portion
12 main portion
15 needle parts
18 flow passage
20 sheath
50 driving section
51 rotation mechanism
52 translation mechanism
100 puncture apparatus
200 blood collecting apparatus
1 central axis of needle body (central axis)

The invention claimed is:
1. A puncture apparatus comprising:
a puncture needle; and
a driving section;
wherein the puncture needle includes:
  a needle body that includes a main portion and a distal portion tapering from the main portion and that is rotatable about a central axis of the needle body,
  the needle body including needle parts which are separated by a boundary along the central axis,
  each of the needle parts being independently translatable along the central axis; and
wherein the driving section includes:
  a rotation mechanism configured to cause the needle body to rotate; and
  a translation mechanism configured to translate each of the needle parts independently along the central axis, the translation mechanism being configured to cause at least one of the needle parts to advance such that the at least one of the needle parts projects forward relative to the other one or more of the needle parts; and
wherein the driving section is configured to cause the needle body to carry out the following two types of motion modes:
(a) first motion mode in which the needle body is caused to rotate and at least one of the needle parts is caused to advance such that the at least one of the needle parts projects forward relative to the other one or more of the needle parts; and
(ii) second motion mode in which the needle body is caused to rotate or at least one of the needle parts is caused to advance such that the at least one of the needle parts projects forward relative to the other one or more of the needle parts.
2. The puncture apparatus as set forth in claim 1, wherein:
the needle body has therein a flow passage which is in communication with an outside environment of the needle body and which allows a fluid to flow therein; and
each of the needle parts forms a part of the flow passage.
3. The puncture apparatus as set forth in claim 1, further comprising a sheath that at least partially covers the needle body,
  the sheath being provided in a proximal portion of the needle body.
4. The apparatus as set as set forth in claim 1, wherein the rotation mechanism is configured to cause the needle body to carry out clockwise rotational motion and counterclockwise rotational motion alternately.

5. The puncture apparatus as set forth in claim 1, wherein a surface of the needle body which surface makes contact with a subject to be punctured is smooth at least in the distal portion.

6. A blood collecting apparatus comprising:
a puncture needle; and
a driving section;
wherein the puncture needle includes:
a needle body that includes a main portion and a distal portion tapering from the main portion and that is rotatable about a central axis of the needle body,
the needle body including needle parts which are separated by a boundary along the central axis,
each of the needle parts being independently translatable along the central axis;
wherein the needle body has therein a flow passage which is in communication with an outside environment of the needle body and which allows a fluid to flow therein, each of the needle parts forms a part of the flow passage; and
wherein the driving section includes:
a rotation mechanism configured to cause the needle body to rotate; and
a translation mechanism configured to translate each of the needle parts independently along the central axis, the translation mechanism being configured to cause at least one of the needle parts to advance such that the at least one of the needle parts projects forward relative to the other one or more of the needle parts; and
wherein the driving section is configured to cause the needle body to carry out the following two types of motion modes:
(a) first motion mode in which the needle body is caused to rotate and at least one of the needle parts is caused to advance such that the at least one of the needle parts projects forward relative to the other one or more of the needle parts; and
(ii) second motion mode in which the needle body is caused to rotate or at least one of the needle parts is caused to advance such that the at least one of the needle parts projects forward relative to the other one or more of the needle parts.

7. The blood collecting apparatus as set forth in claim 6, further comprising a sheath that at least partially covers the needle body,
the sheath being provided in a proximal portion of the needle body.

8. The blood collecting apparatus as set forth in claim 6, wherein the rotation mechanism is configured to cause the needle body to carry out clockwise rotational motion and counterclockwise rotational motion alternately.

9. The blood collecting apparatus as set forth in claim 6, wherein a surface of the needle body which surface makes contact with a subject to be punctured is smooth at least in the distal portion.

* * * * *